(12) United States Patent
Sato

(10) Patent No.: US 6,313,349 B1
(45) Date of Patent: Nov. 6, 2001

(54) AMINOPHENOL COMPOUND, METHOD FOR PRODUCING THE SAME AND INTERMEDIATE IN SYNTHESIZING THE SAME

(75) Inventor: Tadahisa Sato, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/672,041

(22) Filed: Sep. 29, 2000

(30) Foreign Application Priority Data

Sep. 29, 1999 (JP) .................................................. 11-277009
Feb. 22, 2000 (JP) .................................................. 12-044481

(51) Int. Cl.$^7$ .................................................. C07C 211/45
(52) U.S. Cl. ........................................... 564/305; 564/312
(58) Field of Search .................................... 564/305, 312; 568/706, 707

(56) References Cited

FOREIGN PATENT DOCUMENTS 2 549 055    1/1985  (FR) .
A-2-28185    1/1990  (JP) .

OTHER PUBLICATIONS

Journal of Medicinal Chemistry (1997), 40 (4), p 479–485.*
Chem. Res. Toxicol. 1990, 3, 268–280.
Journal of Medicinal Chemistry, 1970, vol. 13, No. 3, 370–376.
J. Chem. Soc., C., 1967, 1053–1054.
Reactive & Functional Polymers 30 (1996) 375–383.
Journal of Polymer Science: Part A: Polymer Chemistry, vol. 36, 1987–1994 (1998).

* cited by examiner

*Primary Examiner*—Sreeni Padmanabhan
*Assistant Examiner*—Sikarl A. Witherspoon
(74) *Attorney, Agent, or Firm*—Sughrue, Mion, Zinn, Macpeak & Seas, PLLC

(57) ABSTRACT

Described are Aminophenol compounds having a nitrogen-linking substituent at the 5-position which are intermediates in synthesizing benzoazole compounds useful as organic luminescence device materials, and a method for producing the same.

15 Claims, No Drawings

AMINOPHENOL COMPOUND, METHOD FOR PRODUCING THE SAME AND INTERMEDIATE IN SYNTHESIZING THE SAME

FIELD OF THE INVENTION

This invention relates to aminophenol compounds and a method for producing the same. More particularly, it relates to aminophenol compounds having a nitrogen-linking substituent at the 5-position which are intermediates in synthesizing benzoazole compounds useful as, for example, organic electroluminescence (EL) materials, and a method for producing the same.

DESCRIPTION OF THE RELATED ART

Tang et al. disclose that compounds having benzoazole skeleton are useful as electron transport compounds and luminous compounds in the electron injection and transport zones of internal junction organic EL devices or host substances doped with a luminous substance in, for example, JP-A-59-194,393 and JP-A-63-264,692 (the term "JP-A" as used herein means "unexamined published Japanese patent application"). Although the compounds having benzoazole skeleton disclosed in these documents are favorable in the capability of showing strong luminescence, these compounds are insufficient in the stability of vacuum evaporation films and electron transport properties. Therefore, devices with the use of these compounds show only extremely insufficient stability for practical use. Under these circumstances, the inventors have conducted intensive studies to find out a molecular structure ensuring improved stability of a luminescence device in compounds with benzoazole skeleton having favorable characteristics of showing strong luminescence.

As a result, they have found out that bisbenzoazole compounds having certain substituents (for example, alkoxy, dialkylamino or diarylamino) show an excellent performance in solving the problem as described above (JP-A-11-29556).

In these studies, it was also found that 2-amino-6-diarylaminophenols (i.e., intermediates in synthesizing bisbenzoazole compounds having a diarylamino group at the 6-position as a substituent) had never been reported and a method for synthesizing these compounds should be originally developed.

Thus, the inventors have studied on the synthesis method and thus tried to produce 2-amino-6-diarylaminophenols. Accordingly, the invention aims at providing a method for producing 2-amino-6-diarylaminophenols and analogs thereof, intermediates in the synthesis thereof, and novel aminophenol compounds which can be produced by the production method.

SUMMARY OF THE INVENTION

As the results of extensive studies, the inventors have found out that the desired compounds can be obtained by reducing compounds obtained by a nucleophilic substitution reaction of certain substituted nitrobenzene compounds. The invention has been completed based on this finding.

Accordingly, the invention provides:

(1) a method for producing an aminophenol compound represented by the following formula (I) via a compound represented by the following formula (II):

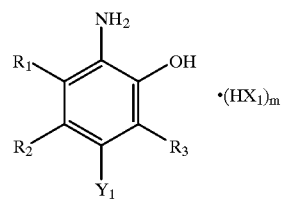

wherein $Y_1$ represents an N-alkyl-N-arylamino group, a diarylamino group, or a five-membered nitrogen-containing aromatic heterocyclic group having an endocyclic nitrogen atom bonded to the benzene ring, provided that when $Y_1$ is a substituted diphenylamino group, it is a diphenylamino group having at least one substituent selected from among alkyl, aryl, alkoxy, aryloxy, dialkylamino, N-alkyl-N-arylamino and diarylamino groups; $R_1$, $R_2$ and $R_3$ represent each a hydrogen atom or a substituent; $X_1$ represents an acid group of an inorganic or organic acid; and m is from 0 to 2; and

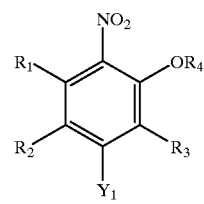

wherein $Y_1$, $R_1$, $R_2$ and $R_3$ are each as defined above; and $R_4$ represents an alkyl group;

(2) an aminophenol compound represented by the following formula (III):

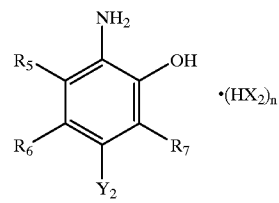

wherein $Y_2$ represents an N-alkyl-N-arylamino group, a diarylamino group, or a five-membered nitrogen-containing aromatic heterocyclic group having an endocyclic nitrogen atom bonded to the benzene ring, provided that when $Y_2$ is a substituted diphenylamino group, it is a diphenylamino group having at least one substituent selected from among alkyl, aryl, alkoxy, aryloxy, dialkylamino, N-alkyl-N-arylamino and diarylamino groups but not an N-(3-methylphenyl)-N-phenylamino group; $R_5$, $R_6$ and $R_7$ represent each a hydrogen atom, a halogen atom, an alkyl group, an aryl group, an alkoxy group or an aryloxy group; $X_2$ represents an acid group of an inorganic or organic acid; and n is from 0 to 2; and (3) a nitrobenzene compound represented by the following formula (IV):

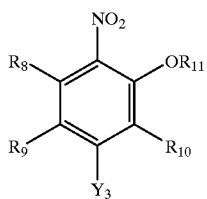

(IV)

wherein $Y_3$ represents an N-alkyl-N-arylamino group, a diarylamino group, or a five-membered nitrogen-containing aromatic heterocyclic group having an endocyclic nitrogen atom bonded to the benzene ring, provided that when $Y_3$ is a substituted diphenylamino group, it is a diphenylamino group having at least one substituent selected from among alkyl, aryl, alkoxy, aryloxy, dialkylamino, N-alkyl-N-arylamino and diarylamino groups; $R_8$, $R_9$ and $R_{10}$ represent each a hydrogen atom, a halogen atom, an alkyl group, an aryl group, an alkoxy group or an aryloxy group; and $R_{11}$ represents a hydrogen atom or an alkyl group.

DETAILED DESCRIPTION OF THE INVENTION

Now, the compounds represented by the formulae (I), (II), (III) and (IV) in the invention will be described in detail.

In the formulae (I) and (II), $Y_1$ represents an N-alkyl-N-arylamino group, a diarylamino group, or a five-membered nitrogen-containing aromatic heterocyclic group having an endocyclic nitrogen atom bonded to the benzene ring. When the diarylamino group is a substituted diphenylamino group, it is a diphenylamino group having at least one substituent selected from among alkyl, aryl, alkoxy, aryloxy, dialkylamino, N-alkyl-N-arylamino and diarylamino groups. More particularly speaking, $Y_1$ represents an optionally substituted N-alkyl-N-arylamino group having from 7 to 40 carbon atoms, an optionally substituted diarylamino group having from 12 to 40 carbon atoms, or an optionally substituted five-membered nitrogen-containing aromatic heterocyclic group having from 4 to 40 carbon atoms and having an endocyclic nitrogen atom bonded to the benzene ring. In the former two groups, substituents on the nitrogen atom may be directly or indirectly bonded to each other to form a five- to seven-membered ring.

The five-membered nitrogen-containing aromatic heterocyclic group may be further condensed with a benzene ring, etc.

Examples of the fundamental structure of $Y_1$ are as follows:

N-Alkyl-N-arylamino groups:

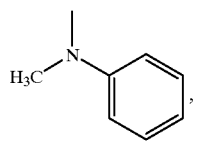, 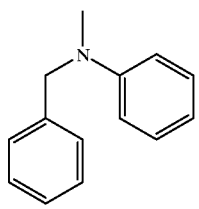, 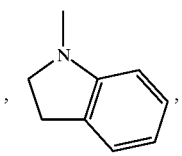,

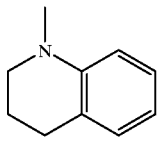

Diarylamino groups:

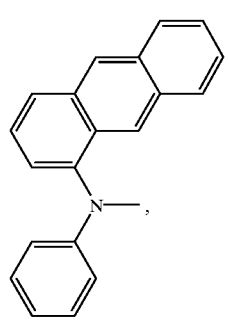

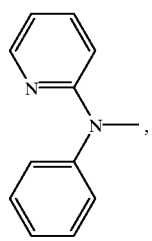

-continued

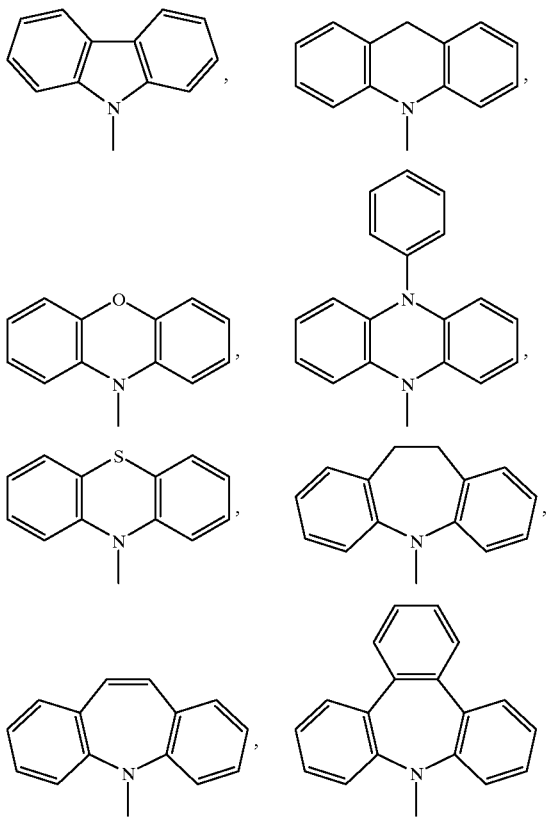

Five-membered nitrogen containing aromatic heterocyclic groups:

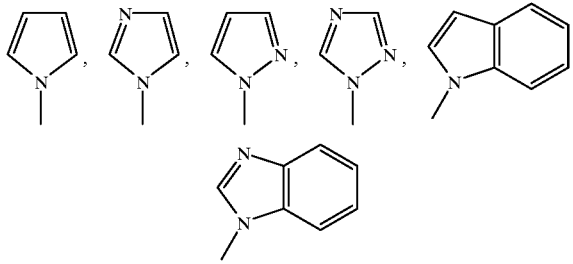

It is preferable that $Y_1$ is a diarylamino group and particularly preferably a diarylamino group forming a five-or seven-membered ring by directly or indirectly bonding the two aryls on the nitrogen atoms.

When $Y_1$ is a group other than a diphenylamino group, it may have the same substituents as the substituents which may be carried by $R_1$ to $R_3$ as will be described hereinafter. Preferable examples of the substituents which may be carried by $Y_1$ other than a diphenylamino group are alkyl, aryl, alkoxy, dialkylamino and diarylamino groups.

When $Y_1$ is a diphenylamino group, it may have substituents such as alkyl, aryl, alkoxy, aryloxy, dialkylamino, N-alkyl-N-arylamino and diarylamino groups. Preferable examples of the substituents are alkyl, aryl and alkyloxy groups and alkyl and aryl groups are still preferable. Particularly preferable examples of the substituents are methyl and phenyl groups.

In the formula (III), $Y_2$ represents an N-alkyl-N-arylamino group, a diarylamino group, or a five-membered nitrogen-containing aromatic heterocyclic group having an endocyclic nitrogen atom bonded to the benzene ring. When $Y_2$ is a substituted diphenylamino group, it is a diphenylamino group having at least one substituent selected from among alkyl, aryl, alkoxy, aryloxy, dialkylamino, N-alkyl-N-arylamino and diarylamino groups but not an N-(3-methylphenyl)-N-phenylamino group. More particularly, $Y_2$ is exemplified by the same groups as defined in $Y_1$ except for not being an N-(3-methylphenyl)-N-phenylamino group. Preferable examples of $Y_2$ include diarylamino groups, still preferably diarylamino groups forming a five- or seven-membered ring.

In the formula (IV), $Y_3$ represents an N-alkyl-N-arylamino group or a diarylamino group. When $Y_2$ is a substituted diphenylamino group, it is a diphenylamino group having at least one substituent selected from among alkyl, aryl, alkoxy, aryloxy, dialkylamino, N-alkyl-N-arylamino and diarylamino groups. More particularly, $Y_3$ is exemplified by the same groups as defined in $Y_1$. Preferable examples of $Y_3$ include diarylamino groups, still preferably diarylamino groups forming a five- or seven-membered ring.

In the formulae (I) and (II), $R_1$, $R_2$ and $R_3$ preferably represent each a hydrogen atom, a halogen atom, an alkyl group, an aryl group, an alkoxy group or an aryloxy group. More particularly, $R_2$, $R_2$ and $R_3$ represent each a hydrogen atom, a halogen atom (fluorine, chlorine, bromine, etc.), an optionally substituted linear or branched alkyl group having 1 to 12 carbon atoms, an optionally substituted aryl group having 6 to 20 carbon atoms, an optionally substituted alkoxy group having 1 to 6 carbon atoms, or an optionally substituted aryloxy group having 6 to 20 carbon atoms. In $R_1$, $R_2$ and $R_3$, adjacent groups may be bonded to each other to form a saturated or unsaturated ring (an aromatic ring, etc.).

Now, the groups as cited above other than hydrogen and halogen atoms will be illustrated in greater detail. Examples of these groups include alkyl groups (for example, methyl, ethyl, n-propyl, n-octyl, n-dodecyl, 2-methoxyethyl, 2-phenylmenthyl, benzyl, isopropyl, isobutyl, s-butyl, t-butyl, t-amyl, t-octyl, cyclopentyl, cyclohexyl, cycloheptyl); aryl groups (for example, phenyl, 2-, 3- or 4-methylphenyl, 4-t-butylphenyl, 4-methoxyphenyl, 4-dimethylaminophenyl, 1- or 2-naphthyl, anthryl, phenanthryl); alkoxy groups (for example, methoxy, ethoxy, n-propoxy, n-butoxy, n-hexyl, isopropoxy, isobutoxy, t-butoxy, cyclopentyloxy, cyclohexyloxy); and aryloxy groups (for example, phenoxy, 2-, 3-or 4-methylphenoxy, 4-t-butylphenoxy, 4-phenylphenoxy, 4-methoxyphenoxy, 2-cyclohexyphenoxy, 3-ethylphenoxy, 1- or 2-naphthoxy, anthryloxy, phenanthryloxy).

When $R_1$ to $R_3$ have substituents, examples of these substituents include halogen atoms, alkyl groups, aryl groups, heterocyclic groups, cyano group, hydroxy group, nitro group, carboxyl group, sulfo group, amino group, alkoxy groups, aryloxy groups, acylamino groups, alkylamino groups, anilino group, ureido group, sulfamoylamino group, alkylthio groups, arylthio groups, alkoxycarbonylamino groups, sulfonamido group, carbamoyl group, sulfamoyl group, sulfonyl group, alkoxycarbonyl group, heterocyclic oxy groups, azo group, acyloxy groups, carbamoyloxy group, silyloxy group, aryloxycarbonylamino group, imido group, heterocyclic thio groups, sulfinyl group, phosphonyl group, aryloxycarbonyl groups, acyl groups, silyl group and azolyl group.

Preferable examples of $R_1$ to $R_3$ include hydrogen atom, alkyl groups and aryl groups and still preferable examples of $R_1$ to $R_3$ include hydrogen atom and alkyl groups.

In the formula (II), $R_4$ represents an alkyl group, more particularly, an alkyl group having 1 to 20 carbon atoms. Preferable examples thereof include methyl, ethyl, butyl, phenylmethyl (benzyl) and naphthylmethyl groups. A methyl or benzyl group is still preferable.

In the formulae (III) and (IV), $R_5$, $R_6$, $R_7$, $R_8$, $R_9$ and $R_{10}$ represent each a hydrogen atom, a halogen atom, an alkyl group, an aryl group, an alkoxy group or an aryloxy group. Particular examples thereof are the same as defined above with respect to $R_1$ to $R_3$ and preferable examples thereof are also the same.

In the formula (IV), $R_{11}$ represents a hydrogen atom or an alkyl group. Particular examples of the alkyl group are the same as defined above with respect to $R_4$. Preferable examples of $R_{11}$ include a hydrogen atom, a methyl group and a benzyl group.

In the formulae (I) and (III), $X_1$ and $X_2$ represent each an acid group of an inorganic or organic acid. Particular examples thereof include inorganic acid groups (for example, hydrochloride, hydrobromide, hydroiodide, sulfate, perchlorate, tetrafluoroborate, hexafluorophosphate) and organic acid groups (for example, acetate, benzoate, methanesulfonate, benzenesulfonate, p-toluenesulfonate). Preferable examples thereof include hydrochloride, sulfate, methanesulfonate and benzenesulfonate and hydrochloride is particularly preferable.

In the formulae (I) and (III), m is from 0 to 2. It is not necessarily an integer. It is preferable that m is 1 or 2.

Now, particular examples of the compounds represented by the formulae (I), (II), (III) and (IV) of the invention will be listed in the following Tables 1, 2, 3 and 4, though the invention is not restricted thereto.

Formula (I)

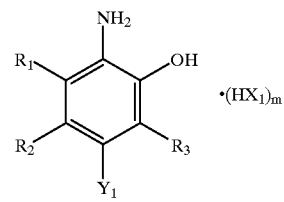

TABLE 1

| No. | $R_1$ | $R_2$ | $R_3$ | $X_1$ | $Y_1$ | m |
|---|---|---|---|---|---|---|
| I-1 | H | H | H | Cl | ![structure: N-methyl-diphenylamine] | 1 |
| I-2 | H | H | H | Cl | ![structure: N-methyl-N-phenyl-3-methylaniline] | 1 |
| I-3 | H | H | H | Cl | ![structure: N-methyl-N-phenyl-4-methylaniline] | 1 |
| I-4 | CH$_3$ | F | H | Br | ![structure: N-methyl-bis(4-methylphenyl)amine] | 1 |
| I-5 | H | H | H | Cl | ![structure: N-methyl-N-phenyl-4-biphenylamine] | 1 |

TABLE 1-continued
| No. | $R_1$ | $R_2$ | $R_3$ | $X_1$ | $Y_1$ | m |
|---|---|---|---|---|---|---|
| I-6 | H | C$_6$H$_5$ | H | Cl | 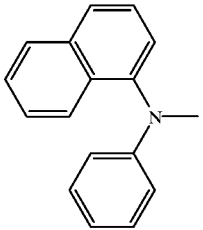 | 1 |
| I-7 | H | H | H | Cl | 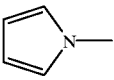 | 1.0 |
| I-8 | H | CH$_3$O | H | Br | 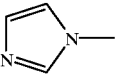 | 1.5 |
| I-9 | H | (c)C$_6$H$_{11}$ | Cl | Cl | 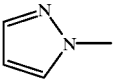 | 1.3 |
| I-10 | H | CH$_3$ | H | Cl | 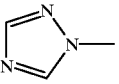 | 1.6 |
| I-11 | C$_6$H$_5$ | H | H | Cl | 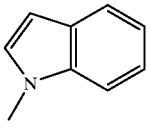 | 1.5 |
| I-12 | H | H | H | Cl | 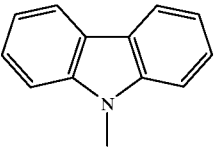 | 1 |
| I-13 | H | H | H | I | 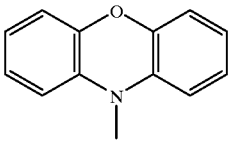 | 1 |
| I-14 | H | H | H | Cl | 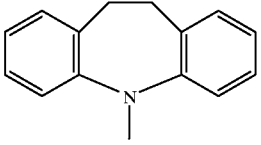 | 1 |
| I-15 | H | H | H | Cl | 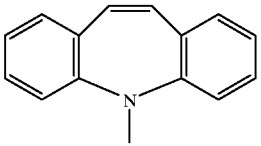 | 1 |

TABLE 1-continued

| No. | R₁ | R₂ | R₃ | X₁ | Y₁ | m |
|---|---|---|---|---|---|---|
| I-16 | H | H | H | Cl | (structure) | 1 |
| I-17 | CF₃ | H | H | Cl | (structure) | 1 |
| I-18 | F | H | H | Cl | (structure) | 1 |
| I-19 | H | H | H | Cl | (structure with CH₃) | 1 |
| I-20 | H | H | H | Cl | (structure with CH₃) | 1 |
| I-21 | H | H | H | Cl | (structure with OCH₃) | 1 |
| I-22 | H | H | H | Cl | —N(C₂H₅)(C₆H₅) | 1.2 |
| I-23 | H | H | H | Cl | —N(CH₃)(naphtyl) | 1.1 |

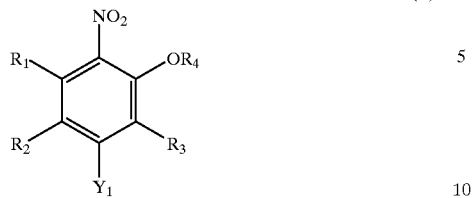
Formula (II)
TABLE 2
| No. | R₁ | R₂ | R₃ | R₄ | Y₁ |
|---|---|---|---|---|---|
| II-1 | H | H | H | CH₂C₆H₅ | N-methyl diphenylamine |
| II-2 | H | H | H | CH₃ | N-methyl diphenylamine |
| II-3 | H | H | H | CH₂C₆H₅ | N-methyl-(3-methylphenyl)phenylamine |
| II-4 | H | H | H | CH₂C₆H₅ | N-methyl-(4-methylphenyl)phenylamine |
| II-5 | CH₃ | F | H | CH₃ | N-methyl-bis(4-methylphenyl)amine |
| II-6 | H | H | H | CH₂C₆H₅ | N-methyl-(4-biphenylyl)phenylamine |

TABLE 2-continued
| No. | R₁ | R₂ | R₃ | R₄ | Y₁ |
|---|---|---|---|---|---|
| II-7 | H | C₆H₅ | H | C₂H₅ | 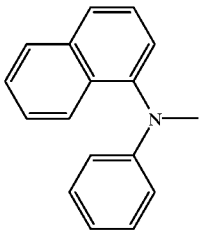 |
| II-8 | H | H | H | CH₂C₆H₅ | 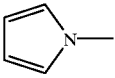 |
| II-9 | H | CH₃O | H | C₃H₇ | 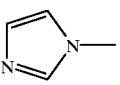 |
| II-10 | H | (c)C₆H₁₁ | Cl | CH₂C₆H₅ | 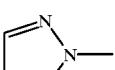 |
| II-11 | H | CH₃ | H | CH₂C₆H₅ | 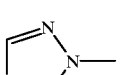 |
| II-12 | C₆H₅ | H | H | CH₂C₆H₅ | 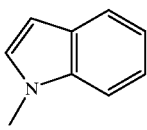 |
| II-13 | H | H | H | CH₂C₆H₅ | 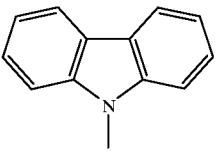 |
| II-14 | H | H | H | CH₃ | 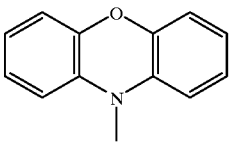 |
| II-15 | H | H | H | CH₃ | 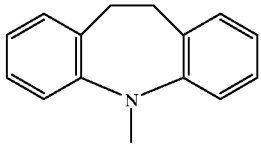 |
| II-16 | H | H | H | CH₃ | 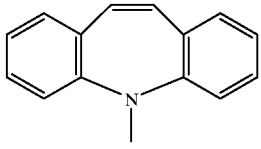 |

TABLE 2-continued

| No. | R$_1$ | R$_2$ | R$_3$ | R$_4$ | Y$_1$ |
|---|---|---|---|---|---|
| II-17 | H | H | H | CH$_2$C$_6$H$_5$ | |
| II-18 | CF$_3$ | H | H | CH$_3$ | |
| II-19 | F | H | H | CH$_2$C$_6$H$_5$ | |
| II-20 | H | H | H | CH$_2$C$_6$H$_5$ | |
| II-21 | H | H | H | CH$_2$C$_6$H$_5$ | |
| II-22 | H | H | H | CH$_2$C$_6$H$_5$ | |
| II-23 | H | H | H | CH$_2$C$_6$H$_5$ | —N(C$_2$H$_5$)(C$_6$H$_5$) |
| II-24 | H | H | H | CH$_2$C$_6$H$_5$ | —N(CH$_3$)(naphtyl) |

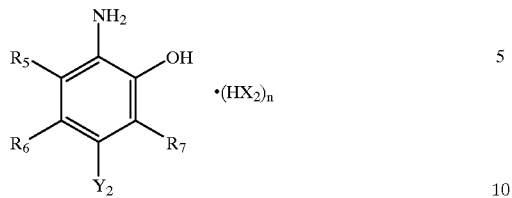
Formula (III)
TABLE 3
| No. | $R_5$ | $R_6$ | $R_7$ | $X_2$ | $Y_2$ | n | Remarks |
|---|---|---|---|---|---|---|---|
| III-1 | H | H | H | Cl | 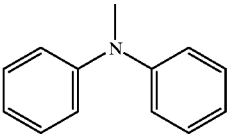 | 1 | Comp. no. (I-1) |
| III-2 | H | H | H | Cl | 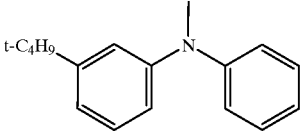 | 1 | |
| III-3 | H | H | H | Cl | 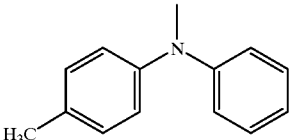 | 1 | (I-3) |
| III-4 | CH$_3$ | F | H | Br | 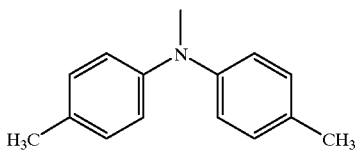 | 1 | (I-4) |
| III-5 | H | H | H | Cl | 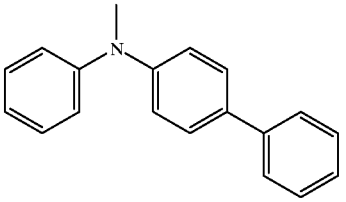 | 1 | (I-5) |
| III-6 | H | C$_6$H$_5$ | H | Cl | 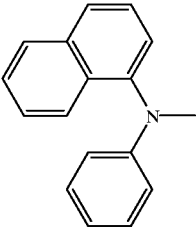 | 1 | (I-6) |
| III-7 | H | H | H | Cl | 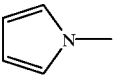 | 1.0 | (I-7) |

TABLE 3-continued
| No. | $R_5$ | $R_6$ | $R_7$ | $X_2$ | $Y_2$ | n | Remarks |
|---|---|---|---|---|---|---|---|
| III-8 | H | CH$_3$O | H | Br | 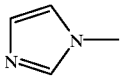 | 1.5 | (I-8) |
| III-9 | H | (c)C$_6$H$_{11}$ | Cl | Cl | 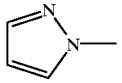 | 1.3 | (I-9) |
| III-10 | H | CH$_3$ | H | Cl | 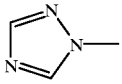 | 1.6 | (I-10) |
| III-11 | C$_6$H$_5$ | H | H | Cl | 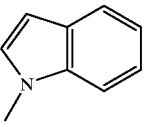 | 1.1 | (I-11) |
| III-12 | H | H | H | Cl | 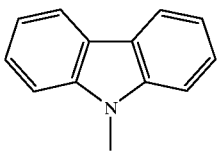 | 1 | (I-12) |
| III-13 | H | H | H | I | 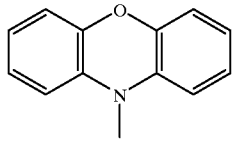 | 1 | (I-13) |
| III-14 | H | H | H | Cl | 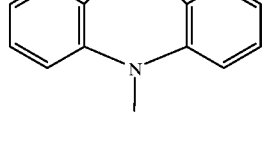 | 1 | (I-14) |
| III-15 | H | H | H | Cl | 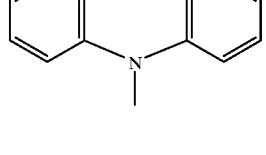 | 1 | (I-15) |
| III-16 | F | H | H | Cl | 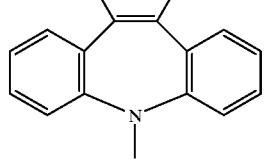 | 1 | (I-16) |

TABLE 3-continued

| No. | $R_5$ | $R_6$ | $R_7$ | $X_2$ | $Y_2$ | n | Remarks |
|---|---|---|---|---|---|---|---|
| III-17 | $CF_3$ | H | H | Cl | (dibenzazepine structure) | 1 | (I-17) |
| III-18 | H | H | H | Cl | (dibenzazepine structure) | 1 | (I-18) |
| III-19 | H | H | H | Cl | (dibenzazepine with $CH_3$) | 1 | (I-19) |
| III-20 | H | H | H | Cl | (dibenzazepine with $CH_3$) | 1 | (I-20) |
| III-21 | H | H | H | Cl | (dibenzazepine with $OCH_3$) | 1 | (I-21) |
| III-22 | H | H | H | Cl | —N($C_3H_7$)($C_6H_5$) | 1.2 | (I-22) |
| III-23 | H | H | H | Cl | —N($CH_3$)(naphtyl) | 1.1 | (I-23) |

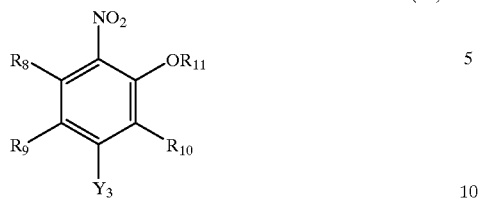
Formula (IV)
TABLE 4
| No. | $R_8$ | $R_9$ | $R_{10}$ | $R_{11}$ | $Y_3$ | Remarks |
|---|---|---|---|---|---|---|
| IV-1 | H | H | H | $CH_2C_6H_5$ | 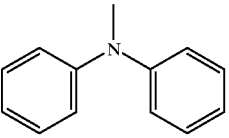 | Comp. no. (II-1) |
| IV-2 | H | H | H | $CH_3$ | 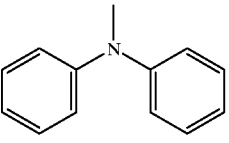 | (II-2) |
| IV-3 | H | H | H | H | 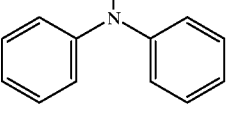 | |
| IV-4 | H | H | H | $CH_2C_8H_5$ | 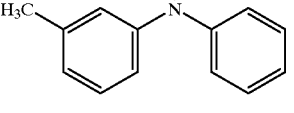 | (II-3) |
| IV-5 | H | H | H | $CH_2C_6H_5$ | 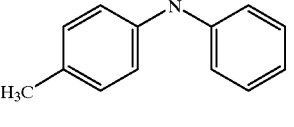 | (II-4) |
| IV-6 | $CH_3$ | F | H | $CH_3$ | 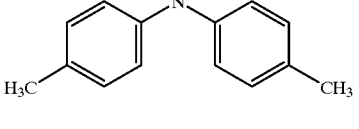 | (II-5) |
| IV-7 | H | H | H | $CH_2C_6H_5$ | 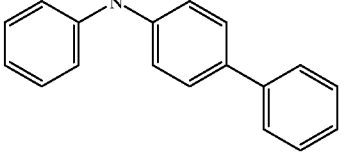 | (II-6) |

TABLE 4-continued
| No. | R₈ | R₉ | R₁₀ | R₁₁ | Y₃ | Remarks |
|---|---|---|---|---|---|---|
| IV-8 | H | C₆H₅ | H | C₂H₅ | 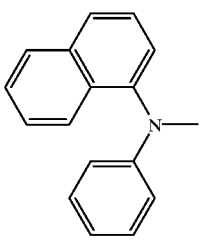 | (II-7) |
| IV-9 | H | H | H | CH₂C₆H₅ | 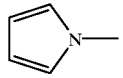 | (II-8) |
| IV-10 | H | CH₃O | H | C₃H₇ | 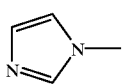 | Comp. no. (II-9) |
| IV-11 | H | (c)C₆H₁₁ | Cl | CH₂C₆H₅ | 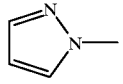 | (II-10) |
| IV-12 | H | CH₃ | H | CH₂C₆H₅ | 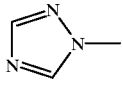 | (II-11) |
| IV-13 | C₆H₅ | H | H | CH₂C₆H₅ | 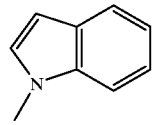 | (II-12) |
| IV-14 | H | H | H | CH₂C₆H₅ | 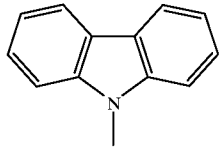 | (II-13) |
| IV-15 | H | H | H | H | 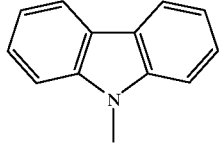 | |
| IV-16 | H | H | H | CH₃ | 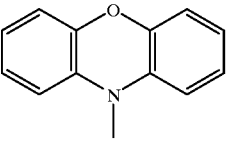 | (II-14) |
| IV-17 | H | H | H | CH₃ | 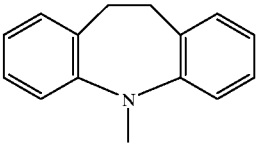 | (II-15) |

TABLE 4-continued
| No. | $R_8$ | $R_9$ | $R_{10}$ | $R_{11}$ | $Y_3$ | Remarks |
|---|---|---|---|---|---|---|
| IV-18 | H | H | H | $CH_3$ | 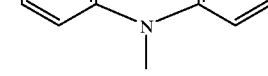 | (II-16) |
| IV-19 | H | H | H | $CH_2C_6H_5$ | 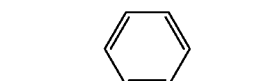 | (II-17) |
| IV-20 | H | H | H | $CH_3$ | 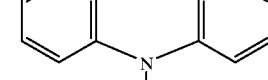 | |
| IV-21 | H | H | H | H | 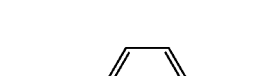 | |
| IV-22 | $CF_3$ | H | H | $CH_3$ | 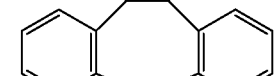 | Comp. no. (II-18) |
| IV-23 | F | H | H | $CH_2C_6H_5$ |  | (II-19) |

TABLE 4-continued
| No. | $R_8$ | $R_9$ | $R_{10}$ | $R_{11}$ | $Y_3$ | Remarks |
|---|---|---|---|---|---|---|
| IV-24 | H | H | H | $CH_2C_6H_5$ | (structure with $CH_3$) | (II-20) |
| IV-25 | H | H | H | $CH_2C_6H_5$ | (structure with $CH_3$) | (II-21) |
| IV-26 | H | H | H | $CH_2C_6H_5$ | (structure with $OCH_3$) | (II-22) |
| IV-27 | H | H | H | $CH_2C_6H_5$ | $-N(C_3H_7)(C_6H_5)$ | (II-23) |
| IV-28 | H | H | H | $CH_2C_6H_5$ | $-N(CH_3)$(naphtyl) | (II-24) |
Next, a method for producing the compounds of the invention will be described. A typical production route is as follows.
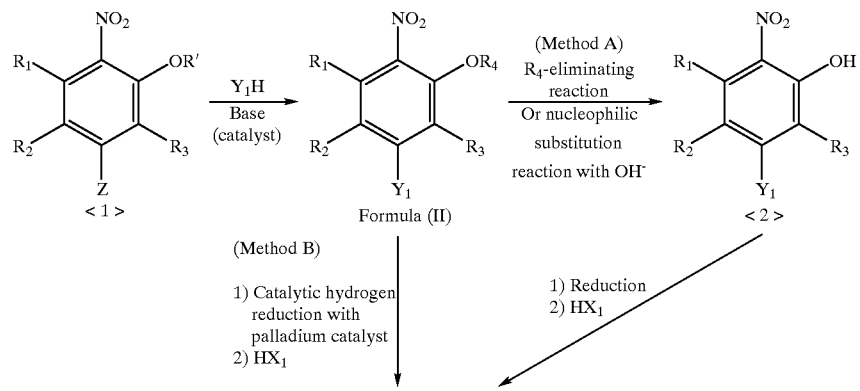

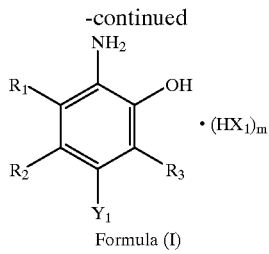

Formula (I)

In the above production route, $R_1$ to $R_4$, $X_1$, $Y_1$ and m are each as defined above; and Z represents a halogen atom.

In case where Z is a fluorine atom, the reaction from the compound <1> to the compound of the formula (II), which is an aromatic nucleophilic substitution reaction, can be smoothly performed in general merely by using a base. In case where Z is a halogen atom other than fluorine, the reaction speed varies depending on the disubstituted amine compound employed as the reactant. When the reaction proceeds slowly, it is frequently effective to use, as a catalyst, copper (Ullman reaction) or palladium. As the reaction solvent, it is preferable to use an amide solvent such as acetamide (DMAc) or 1,3-dimethyl-2-imidazolidinone (DMI) or an aromatic or aliphatic hydrocarbon solvent such as toluene, xylene or decalin.

The characteristic of the invention resides in that the compound of the formula (I) is produced via the compound of the formula (II). There are two methods for converting the compound (II) into the compound (I). In one of these methods, the compound (II) is converted into the compound (I) via the compound <2> (method A), while the compound (II) is directly converted into the compound (I) in the other method (method B).

In the method A, nitro group is reduced after converting —$OR_4$ group into —OH group, i.e., via the compound <2>. The compound <2> can be obtained by converting —$OR_4$ group into —OH group through: (1) a demethylation reaction with the use of, for example, $H_2SO_4$, HBr, $AlCl_3$, $BBr_3$, RSNa, LiI/collidine or TMSI; or (2) a nucleophilic substitution reaction into a benzene ring by hydroxyl ion with the use of, for example, KOH.

The method (1) is performed by reference to documents. Typical examples of such documents include Org. Synth. I, 150(1941), J. Org. Chem., 27, 2037(1962), Org. Synth., V, 412(1973), Tetrahedron Lett., 1970, 1327, Chem. Commun., 1969, 616 and J. Org. Chem., 42, 3761(1977). Favorable examples thereof are the method with the use of a protonic acid (for example, $H_2SO_4$, HBr) and the method with the use of LiI/collidine. Now, the former method will be described in detail. The compound (II) is heated together with a protonic acid (for example, $H_2SO_4$, HBr) in water, acetic acid or a mixture thereof. The protonic acid is employed in an amount of at least 1 equivalent, preferably 1 to 10 equivalents, to the substrate represented by the formula (II). The reaction temperature ranges from 20 to 120° C., preferably from 50 to 100° C. The reaction time ranges from 0.5 to 24 hours, preferably from 1 to 5 hours.

Next, the latter method will be described in detail. In this method, the compound (II) is heated together with LiI in the presence of a base such as collidine. This reaction may be carried out in the presence of an organic solvent such as toluene. Alternatively, it may be performed by using the base as a solvent without resort to any other organic solvents. The LiI is employed in an amount of at least 1 equivalent, preferably 1 to 10 equivalents, to the substrate represented by the formula (II). The base is employed in an amount of at least 1 equivalent, preferably at least 5 equivalents, to the substrate represented by the formula (II). The reaction temperature ranges from 20 to 300° C., preferably from 100 to 200° C. The reaction time ranges from 0.5 to 24 hours, preferably from 1 to 10 hours.

Now, the method (2) will be described in detail. In this method, the compound (II) is reacted with an alkali hydroxide such as KOH in water, an aqueous alcohol or an ether solvent. Particular examples of the alcohol and ether solvents include alcohol solvents such as methanol, ethanol, isopropanol, ethylene glycol and methoxyethanol, and ether solvents such as dibutyl ether, t-butyl methyl ether, tetrahydrofuran (THF) and dioxane. The alkali hydroxide is employed in an amount of at least 1 equivalent, preferably 1 to 10 equivalents, to the substrate represented by the formula (II). The reaction temperature ranges from 0 to 100° C., preferably from 20 to 80° C. The reaction time ranges from 0.5 to 30 hours, preferably from 1 to 8 hours.

The procedure for isolating the compound <2> varies depending on its crystallinity. In case of having a good crystallinity, the compound <2> can be isolated in the form of crystals by neutralizing in an aqueous solvent. In case of having only a poor crystallinity, it is isolated by extraction. The compound <2> may be reduced into the compound represented by the formula (I) either after the completion of the purification or without carrying out any purification.

The conversion of the compound <2> into the compound (I) through the reduction of nitro group can be carried out by using commonly known methods such as metal reduction or catalytic hydrogen reaction. In the metal reduction, it is preferable to use iron. In this case, the reduction is performed in a solvent mixture of an alcohol solvent (for example, isopropanol) with water. When the compound <2> has a poor solubility, use may be made of an amide solvent (for example, dimethylformamide, dimethylacetamide) as an auxiliary solvent. Reduced iron is used in an amount of at least 8 equivalents, preferably from 10 to 20 equivalents, to the compound <2>. The reduction may be performed under neutral (with the addition of a small amount of ammonium chloride to activate iron) or acidic conditions, though neutral conditions are preferred.

The catalytic hydrogen reduction method is exemplified by the method with a nickel or palladium catalyst using hydrogen gas, the method with a palladium catalyst using a formate or hydrazine as a hydrogen donor, and the method with a catalytic amount of iron (II) chloride catalyst using hydrazine as a hydrogen donor. Preferable examples of this method include the method with a Raney nickel or palladium-carbon catalyst using hydrogen gas, and the method with tetrakis(tirphenylphosphine) palladium (0) complex or a palladium-carbon catalyst using a formate. As the solvent, use may be made of alcohol solvents, ether solvents, ester solvents or amide solvents. Among all, it is preferable to use an alcohol solvent such as methanol, ethanol or isopropanol. In the catalytic hydrogen reduction, the catalyst is used in an amount of from 0.01 to 20% by mol, preferably form 0.1 to 2% by mol, based on the substrate. The reaction temperature ranges from 0 to 150° C., preferably from 20 to 100° C. The reaction time ranges from 0.5 to 24 hours, preferably from 1 to 10 hours.

In the method B which is effective in case where $R_4$ is an aryl-substituted methyl group such as benzyl, catalytic hydrogen reduction is performed mainly by using a palladium catalyst. The catalytic hydrogen reduction method with the use of a palladium catalyst is exemplified by the method with the use of hydrogen gas as a hydrogen source, and the method with the use of formic acid or a formate such as ammonium formate. An appropriate method may be selected. As the solvent, use may be made of alcohol solvents, ether solvents, ester solvents or amide solvents. Among all, it is preferable to use an alcohol solvent such as methanol, ethanol or isopropanol. The catalyst is used in an amount of from 0.01 to 20% by mol, preferably form 0.1 to 2% by mol, based on the substrate. The reaction temperature ranges from 0 to 150° C., preferably from 20 to 100° C. The reaction time ranges from 0.5 to 24 hours, preferably from 1 to 10 hours.

Since the reduced compound (i.e., the compound represented by the formula (I) wherein m is 0) is liable to undergo oxidative decomposition, the compound according to the invention is purified by converting it into an acid salt, immediately after the isolation (for example, extraction), followed by crystallization. In case where a compound of m=O is needed, it is preferable that the product is obtained by neutralizing an acid salt.

EXAMPLES

Now, the invention will be illustrated in greater detail by reference to the following Examples. However, it is to be understood that the invention is not construed as being limited thereto.

Example 1
Synthesis of Compound (I-1) via Compound (II-1)

5.4 g (32.1 mmol) of diphenylamine was dissolved in 50 ml of 1,3-dimethyl-2-imidazolidinone (DMI) and stirred under cooling in an ice-bath. Next, 3.6 g (32.1 mmol) of t-BuOK was added thereto. Subsequently, 7.2 g (29.2 mmol) of 2-benzyloxy-4-fluoronitrobenzene (obtained by benzylation of commercially available 5-fluoro-2-nitrophenol) dissolved in 5 ml of DMI was dropped thereinto. After the completion of the dropping, the ice-bath was taken off and the mixture was allowed to stand at room temperature overnight. Next, the liquid reaction mixture was poured into water and extracted with ethyl acetate thrice. After washing with water, drying and concentrating under reduced pressure, the residue was recrystallized from methanol containing a small amount of acetonitrile. Thus, 7.2 g (yield 62%) of the compound (II-1) (2-benzyloxy-4-diphenylaminonitrobenzene) could be obtained as yellow powdery crystals.

6.0 g (15.1 mmol) of the compound (II-1) was dissolved in 50 ml of methanol and 100 mg of a palladium-carbon catalyst was added thereto. Thus catalytic hydrogen reduction was performed under 10 kg/cm² at 30 to 40° C. After 1 hour, the catalyst was filtered off through celite and 1.5 ml (about 18 mmol) of conc. hydrochloric acid was added. Then the mixture was concentrated in an evaporator under reduced pressure and the residue was recrystallized from acetonitrile. Thus, 3.3 g (yield 70%) of the compound (I-1) could be obtained as pale gray crystals.

NMR(CDCl$_3$+small amount of DMSO-d$_6$)
δ(ppm) 6.52(1H, d, J=9.0), 6.70(1H, s), 7.00(2H, t, J=7.0), 7.05(4H, d, J=7.0), 7.22(4H, t, J=7.0), 7.30(1H, d, J=9.0), 9.5–10.1 (4H).

Example 2
Synthesis of Compound (I-1) via Compounds (II-2), (IV-3), etc.

5.4 g (32.1 mmol) of diphenylamine was dissolved in 50 ml of 1,3-dimethyl-2-imidazolidinone (DMI) and stirred under cooling in an ice-bath. Next, 3.6 g (32.1 mmol) of t-BuOK was added thereto. Subsequently, 5.0 g (29.2 mmol) of 2-methoxy-4-fluoronitrobenzene (obtained by methylation of commercially available 5-fluoro-2-nitrophenol) dissolved in 5 ml of DMI was dropped thereinto. After the completion of the dropping, the ice-bath was taken off and the mixture was allowed to stand at room temperature overnight. Next, the liquid reaction mixture was poured into water and extracted with ethyl acetate thrice. After washing with water, drying and concentrating under reduced pressure, the residue was recrystallized from methanol containing a small amount of acetonitrile. Thus, 6.0 g (yield 65%) of the compound (II-2) (2-methoxy-4-diphenylaminonitrobenzene) could be obtained as yellow powdery crystals.

4.5 g (14.0 mmol) of the compound (II-2) was dissolved in 50 ml of acetic acid and 20 ml of 47% HBr was added thereto. After stirring while heating under flux for about 5 hours, the mixture was extracted with ethyl acetate. The extract was dried, filtered and concentrated in an evaporator under reduced pressure. The residue, which was a crude product (i.e., being contaminated with a by-product suffering from partial bromination at aminophenolbenzene nucleus) of the compound (IV-3) (5-diphenylamino-2-nitrophenol), was dissolved in 100 ml of N,N-dimethylformamide. 7.5 ml (200 mmol) of formic acid, 41.8 ml (300 nmol) of triethylamine and 350 mg (0.3 mmol) of tetrakis(triphenylphosphine) palladium (0) were added thereto and the resultant mixture was stirred at 80° C. for 5 hours. Then water was added to the liquid reaction mixture for extraction. After concentrating under reduced pressure without drying, the residue was dissolved in 50 ml of methanol. Then 3.0 ml (about 36 mmol) of conc. hydrochloric acid was added and the mixture was concentrated in an evaporator under reduced pressure. Next, the residue (wherein bromine in the aminophenolbenzene nucleus had been completely reduced under the reduction conditions described above) was recrystallized from acetonitrile. Thus, 2.6 g (yield 60%) of the compound (I-1) could be obtained as pale gray crystals.

Example 3
Synthesis of Compound (I-1) via Compounds (II-2) and (IV-3)

43.0 g (134 mmol) of the compound (II-2) obtained by the method of Example 2 was introduced into a flask and 32.3 g (240 mmol) of LiI, 81.7 g (670 mmol) of collidine and 430 ml of toluene were added thereto. The obtained mixture was heated under reflux while stirring for 5 hours, though a precipitate was formed during the heating/refluxing. Then it was cooled to room temperature and allowed to stand overnight. The crystalline precipitate was filtered by suction and washed with toluene. Then it was transferred into a beaker and acidified by adding water and 2N hydrochloric acid followed by stirring at room temperature for 2 hours. The crystals were filtered, washed with water and dried at about 50° C. Thus, 40.5 g (yield 98.7%) of the compound (IV-3) (5-diphenylamino-2-nitrophenol) was obtained.

59.0 g (1.06 mmol) of reduced iron was introduced into a flask and 80 ml of water and 200 ml of isopropanol were added thereto. After further adding 2.1 g (39.3 mmol) of ammonium chloride, the mixture was heated and refluxed under a nitrogen gas stream for about 30 minutes. 40.5 g (132 mmol) of the compound (IV-3), as crystals, was added in 2 or 3 portions thereto (at each point of the addition, the heating/refluxing was temporarily stopped). Further, about 100 ml of isopropanol was added and the heating/refluxing was continued, while monitoring the progress of the reaction by TLC. When the starting material disappeared (after about 1 hour), the heating/refluxing was ceased. After cooling to about 50° C., the reaction mixture was filtered through celite. The filtrate was cooled to room temperature and then extracted with ethyl acetate. Next, 12.5 ml (about 150 mmol) of conc. hydrochloric acid was added to the extract and the mixture was concentrated in an evaporator under reduced pressure. The residue was recrystallized from acetonitrile and thus 33.0 g (yield 80%) of the compound (I-1) could be obtained as pale gray crystals.

Example 4
Synthesis of Compound (I-12) via Compound (II-13)

The compound (I-12) could be obtained (yield 67%) as pale bluish gray crystals in the same manner as in Example 1 except for substituting the diphenylamine by carbazole in the molar equivalent amount. The elemental analysis data indicated that this product was a monohydrochloride. M.p.: to 100° C. (decomp.).

Example 5
Synthesis of Compound (I-16) via Compound (II-17)

The compound (16) could be obtained (yield 55%) as pale bluish gray crystals in the same manner as in Example 1 except for substituting the diphenylamine by 9H-tribenzo[b,d,f] azepine in the molar equivalent amount. The elemental analysis data indicated that this product was a monohydrochloride. M.p.: to 85° C. (decomp.).

Bisbenzoxazole compounds synthesized by using the aminophenol compounds according to the invention are excellent in vacuum evaporation properties and serve, in organic electroluminescence device, as electron transporters having a high device stability and excellent luminance characteristics. The invention has facilitated the acquisition of aminophenol compounds and thus promoted studies on organic electroluminescence devices.

The entire disclosure of each and every foreign patent application from which the benefit of foreign priority has been claimed in the present application is incorporated herein by reference, as if fully set forth.

What is claimed is:

1. A method for producing an aminophenol compound represented by the following formula (I) via a compound represented by the following formula (II):

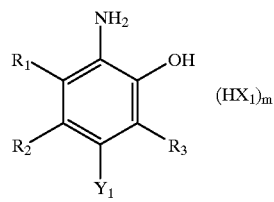

(I)

wherein $Y_1$, represents an N-alkyl-N-arylamino group, a diarylamino group, or a five-membered nitrogen-containing aromatic heterocyclic group having an endocyclic nitrogen atom bonded to the benzene ring, provided that when $Y_1$ is a substituted diphenylamino group, it is a diphenylamino group having at least one substituent selected from a group consisting of alkyl, aryl, alkoxy, aryloxy, dialkylamino, N-alkyl-N-arylamino and diarylamino groups; $R_1$, $R_2$ and $R_3$ each represents a hydrogen atom or a substituent; $X_1$ represents an acid group of an inorganic or organic acid; and m is from 0 to 2; and

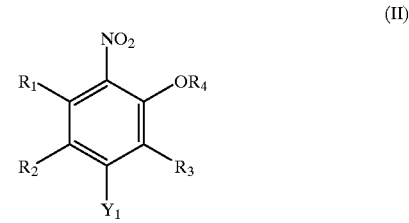

(II)

wherein $Y_1$, $R_1$, $R_2$, and $R_3$ are each as defined above; and $R_4$ represents an alkyl group, comprising one of the following methods (a) and (b):
(a) converting the —$OR_4$ group in formula (II) into an —OH group by using a dealkylation reaction or a nucleophilic substitution reaction into a benzene ring by hydroxyl ion,
reducing the nitro group in formula (II) by using a metal reduction method or a catalytic hydrogen reduction method, and
treating the product with $HX_1$,
when $R_4$ in the formula (II) is an unsubstituted alkyl group;
(b) subjection the compound represented by formula (II) to catalytic hydrogen reduction by using a palladium catalyst, and
treating the product with $HX_1$,
when $R_4$ is an aryl-substituted methyl group.

2. The method as claimed in claim 1, wherein $Y_1$ represents a substituted or unsubstituted N-alkyl-N-arylamino group having 7 to 40 carbon atoms, a substituted or unsubstituted diarylamino group having 12 to 40 carbon atoms, or a substituted or unsubstituted five-membered nitrogen-containing aromatic heterocyclic group having an endocyclic nitrogen atom bonded to the benzene ring.

3. An aminophenol compound represented by the following formula (III):

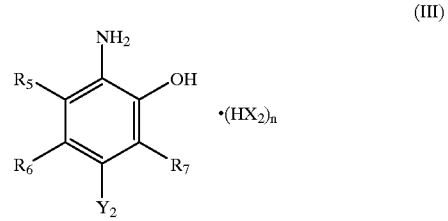

(III)

wherein $Y_2$ represents an N-alkyl-N-arylamino group, a diarylamino group, or a five-membered nitrogen-containing aromatic heterocyclic group having an endocyclic nitrogen atom bonded to the benzene ring, provided that when $Y_2$ is a substituted diphenylamino group, it is a diphenylamino group having at least one substituent selected from a group consisting of alkyl, aryl, alkoxy, aryloxy, dialkylamino, N-alkyl-N-arylamino and diarylamino groups but not an N-(3-methylphenyl)-N-phenylamino group; $R_5$, $R_6$ and $R_7$ each represents a hydrogen atom, a halogen atom, an alkyl group, an aryl group, an alkoxy group or an aryloxy group; $X_2$ represents an acid group of an inorganic or organic acid; and n is from 0 to 2.

4. The aminophenol compound as claimed in claim 3, wherein $Y_2$ represents a substituted or unsubstituted N-alkyl-N-arylamino group having 7 to 40 carbon atoms, a substituted or unsubstituted diarylamino group having 12 to 40 carbon atoms, or a substituted or unsubstituted five-membered nitrogen-containing aromatic heterocyclic group having an endocyclic nitrogen atom bonded to the benzene ring.

5. A nitrobenzene compound represented by the following formula (IV):

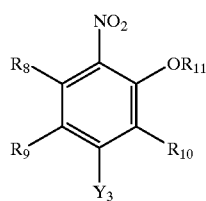

(IV)

wherein $Y_3$ represents an N-alkyl-N-arylamino group or a diarylamino group, provided that when $Y_3$ is a substituted diphenylamino group, it is a diphenylamino group having at least one substituent selected from among alkyl, aryl, alkoxy, aryloxy, dialkylamino, N-alkyl-N-arylamino and diarylamino groups; $R_8$, $R_9$, and $R_{10}$ each represents a hydrogen atom, a halogen atom, an alkyl group, an aryl group, an alkoxy group or an aryloxy group; and $R_{11}$ represents a hydrogen atom or an alkyl group.

6. A nitrobenzene compound as claimed in claim 5, wherein $Y_3$ represents a substituted or unsubstituted N-alkyl-N-arylamino group having 7 to 40 carbon atoms or a substituted or unsubstituted diarylamino group having 12 to 40 carbon atoms.

7. The method as claimed in claim 1, wherein the dealkyklation reaction is carried out by using one of a protonic acid and Li/collidine.

8. The method as claimed in claim 7, wherein the dealkylation reaction is carried out by heating the compound represented by formula (II) together with the protonic acid in one of water, acetic acid and a mixture thereof.

9. The method as claimed in claim 8, wherein the protonic acid is used in an equimolar or more amount of the compound represented by the formula (II).

10. The method as claimed in claim 7, wherein the dealkylation reaction is carried out by heating the compound represented by formula (II) together with a base including LiI, and the LiI is used in an equimolar or more amount of the compound represented by the formula (II).

11. The method as claimed in claim 10, wherein the base is used in an equimolar or more amount of the compound represented by the formula (II).

12. The method as claimed in claim 1, wherein the nucleophilic substitution reaction is carried out by reacting the compound represented by the formula (II) with an alkali hydroxide in one of water, an aqueous alcohol and an ether solvent.

13. The method as claimed in claim 12, wherein the alkali hydroxide is used in an equimolar or more amount of the compound represented by the formula (II).

14. The method as claimed in claim 1, wherein when $R_4$ is an aryl-substituted methyl group, a hydrogen gas is used as a hydrogen source, or a formic acid or a formate is used, in the catalytic hydrogen reduction.

15. The method as claimed in claim 1, wherein in (a), the metal reduction method is an iron reduction, and the catalytic hydrogen reduction method is one using a nickel or palladium catalyst and a hydrogen gas, one using a palladium catalyst and a formate or hydrazine as a hydrogen donor, or one using a catalytic amount of iron (II) chloride catalyst and a hydrazine as a hydrogen donor.

* * * * *